(12) United States Patent
Freeberg

(10) Patent No.: US 7,801,620 B2
(45) Date of Patent: Sep. 21, 2010

(54) RF TELEMETRY LINK QUALITY ASSESSMENT SYSTEM AND METHOD

(75) Inventor: Scott Freeberg, Birchwood Village, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 868 days.

(21) Appl. No.: 11/214,508

(22) Filed: Aug. 29, 2005

(65) Prior Publication Data

US 2007/0049983 A1 Mar. 1, 2007

(51) Int. Cl.
 *A61N 1/08* (2006.01)
(52) U.S. Cl. .......................... 607/60; 607/32
(58) Field of Classification Search .................... 607/60, 607/32
 See application file for complete search history.

(56) References Cited

U.S. PATENT DOCUMENTS

| | | | |
|---|---|---|---|
| 4,633,411 A | 12/1986 | Bliss | |
| 4,799,059 A | 1/1989 | Grindahl et al. | |
| 5,342,408 A | 8/1994 | deCoriolis et al. | |
| 5,394,433 A | 2/1995 | Bantz et al. | |
| 5,562,713 A | 10/1996 | Silvian | |
| 5,603,088 A | 2/1997 | Gorday et al. | |
| 5,612,960 A | 3/1997 | Stevens et al. | |
| 5,617,871 A | 4/1997 | Burrows | |
| 5,683,432 A | 11/1997 | Goedeke et al. | |
| 5,729,680 A | 3/1998 | Belanger et al. | |
| 5,752,977 A | 5/1998 | Grevious et al. | |
| 5,843,139 A | 12/1998 | Goedeke et al. | |
| 6,031,863 A | 2/2000 | Jusa et al. | |
| 6,088,381 A | 7/2000 | Myers, Jr. | |
| 6,130,905 A | 10/2000 | Wakayama | |
| 6,223,083 B1 | 4/2001 | Rosar | |
| 6,243,568 B1 | 6/2001 | Detef et al. | |

(Continued)

FOREIGN PATENT DOCUMENTS

EP 1308184 A2 5/2003

(Continued)

OTHER PUBLICATIONS

"U.S. Appl. No. 11/039,200 Non Final office action mailed Aug. 3, 2006", 10 pgs.

(Continued)

*Primary Examiner*—Carl H Layno
*Assistant Examiner*—Natasha N Patel
(74) *Attorney, Agent, or Firm*—Schwegman, Lundberg & Woessner, P.A.

(57) ABSTRACT

A system and method for assessing link quality for radio frequency (RF) transmissions between a programmer and an implantable medical device (IMD) is provided. An embodiment of the method includes measuring a plurality of available wireless communication channel potentially used to communicate between an implantable medical device (IMD) and a programmer to determine signal and noise levels for the channels. The method also includes storing the signal and noise levels. The method further includes processing the stored levels to determine the interference potential on the channels adjacent to the available channels. In this embodiment, the method also includes selecting a preferred communication channel based on a function of noise level for a target center channel and interference potential for corresponding adjacent channels to the target channel. Other aspects and embodiments are provided herein.

20 Claims, 4 Drawing Sheets

U.S. PATENT DOCUMENTS

| | | | |
|---|---|---|---|
| 6,381,492 | B1 | 4/2002 | Rockwell et al. |
| 6,424,867 | B1 | 7/2002 | Snell et al. |
| 6,443,891 | B1 | 9/2002 | Grevious |
| 6,471,645 | B1 | 10/2002 | Warkentin et al. |
| 6,535,763 | B1 | 3/2003 | Hiebert et al. |
| 6,535,766 | B1 * | 3/2003 | Thompson et al. ............ 607/60 |
| 6,600,952 | B1 | 7/2003 | Snell et al. |
| 6,631,296 | B1 | 10/2003 | Parramon et al. |
| 6,763,269 | B2 | 7/2004 | Cox |
| 6,801,807 | B2 | 10/2004 | Abrahamson |
| 6,868,288 | B2 | 3/2005 | Thompson |
| 6,897,788 | B2 | 5/2005 | Khair et al. |
| 6,978,181 | B1 | 12/2005 | Snell |
| 6,985,773 | B2 | 1/2006 | Von Arx et al. |
| 7,013,178 | B2 | 3/2006 | Reinke et al. |
| 7,146,134 | B2 | 12/2006 | Moon et al. |
| 7,177,700 | B1 | 2/2007 | Cox |
| 7,218,969 | B2 | 5/2007 | Vallapureddy et al. |
| 7,280,872 | B1 | 10/2007 | Mosesov et al. |
| 7,289,853 | B1 | 10/2007 | Campbell et al. |
| 2001/0012955 | A1 | 8/2001 | Goedeke et al. |
| 2002/0109621 | A1 | 8/2002 | Khair et al. |
| 2002/0123672 | A1 | 9/2002 | Christophersom et al. |
| 2002/0143372 | A1 | 10/2002 | Snell et al. |
| 2002/0183806 | A1 | 12/2002 | Abrahamson et al. |
| 2003/0097157 | A1 | 5/2003 | Wohlgemuth et al. |
| 2003/0114891 | A1 | 6/2003 | Hiebert et al. |
| 2003/0146835 | A1 | 8/2003 | Carter |
| 2003/0187484 | A1 | 10/2003 | Davis et al. |
| 2004/0127959 | A1 | 7/2004 | Amundson et al. |
| 2004/0167587 | A1 | 8/2004 | Thompson |
| 2004/0176811 | A1 | 9/2004 | Von Arx et al. |
| 2004/0176822 | A1 | 9/2004 | Thompson et al. |
| 2005/0245992 | A1 | 11/2005 | Persen et al. |
| 2006/0030903 | A1 | 2/2006 | Seeberger et al. |
| 2006/0161222 | A1 | 7/2006 | Haubrich et al. |
| 2006/0161223 | A1 | 7/2006 | Vallapureddy et al. |
| 2006/0195161 | A1 | 8/2006 | Li |
| 2006/0195162 | A1 | 8/2006 | Arx et al. |
| 2007/0185550 | A1 | 8/2007 | Vallapureddy et al. |
| 2007/0260293 | A1 | 11/2007 | Carpenter et al. |
| 2008/0015655 | A1 | 1/2008 | Bange et al. |
| 2008/0015656 | A1 | 1/2008 | Bange et al. |
| 2008/0228237 | A1 | 9/2008 | Bange et al. |

FOREIGN PATENT DOCUMENTS

| | | | |
|---|---|---|---|
| WO | WO-9819400 | A1 | 5/1998 |
| WO | WO-2008008564 | A2 | 1/2008 |
| WO | WO-2008008564 | A3 | 1/2008 |
| WO | WO-2008008565 | A2 | 1/2008 |
| WO | WO-2008008565 | A3 | 1/2008 |
| WO | WO-2008027655 | A1 | 3/2008 |
| WO | WO-2008112222 | A2 | 9/2008 |

OTHER PUBLICATIONS

"U.S. Appl. No. 11/039,200 Notice of allowance mailed Dec. 15, 2006", 4 pgs.

"U.S. Appl. No. 11/039,200 Response filed Nov. 2, 2006 to Non Final office action mailed Aug. 3, 2006", 9 pgs.

"U.S. Appl. No. 11/456,937, Non-Final Office Action mailed Jul. 31, 2008", 13 pgs.

"U.S. Appl. No. 11/456,937, Response filed Oct. 15, 2008 to Non Final Office Action mailed Jul. 31, 2008", 10 pgs.

"U.S. Appl. No. 11/456,942, Non-Final Office Action mailed Aug. 18, 2008", 15 pgs.

"U.S. Appl. No. 11/456,942, Response filed Nov. 18, 2008 to Non Final Office Action mailed Aug. 18, 2008", 10 pgs.

"International Application Serial No. PCT/US2007/003216, International Search Report mailed Sep. 12, 2008", 4 pgs.

"International Application Serial No. PCT/US2008/003216, Written Opinion mailed Sep. 12, 2008", 8 pgs.

"PCT Application No. PCT/US2007/069424, International Search Report mailed Dec. 27, 2007", 4 pgs.

"PCT Application No. PCT/US2007/069424, Written Opinion mailed Dec. 27, 2007", 9 pgs.

"PCT Application No. PCT/US2007/069426, International Search Report mailed Dec. 27, 2007", 4 pgs.

"PCT Application No. PCT/US2007/069426, Written Opinion mailed Dec. 27, 2007", 8 pgs.

Adams, J. T, "An introduction to IEEE STD 802.15.4", *Aerospace conference, 2006 IEEE big sky*, (Mar. 4-11, 2006), 1-8.

Bange, Joseph E, et al., "Implantable Medical Device Telemetry With Adaptive Frequency Hopping", U.S. Appl. No. 11/456,937, filed Jul. 12, 2006, 35 pages.

Bange, Joseph E, et al., "Implantable Medical Device Telemetry With Periodic Frequency Hopping", U.S. Appl. No. 11/456,942, filed Jul. 12, 2006, 43 Pages.

Duflot, M., et al., "A formal analysis of bluetooth device discovery", *International journal on software tools for technology transfer*, 8 (6), (Jul. 5, 2006), 621-632.

Golmie, N., et al., "The Evolution of Wireless LANs and PANs -Bluetooth and WLAN coexistence: challenges and solutions", *IEEE Personal Communications*, 10(6), (Dec. 2003), 22-29.

Zhu, H., et al., "A survey of quality of service in IEEE 802.11 Networks", *IEEE Wireless Comunications, IEEE Service Center*, Piscataway, NJ, US, 11(4), (Aug. 2004), 6-14 pgs.

"U.S. Appl. No. 11/456,937, Response filed Feb. 23, 2009 to Final Office Action mailed Dec. 22, 2008", 9 pgs.

"U.S. Appl. No. 11/456,937 Advisory Action mailed Mar. 12, 2009", 3 pgs.

"U.S. Appl. No. 11/456,937, Response filed Apr. 21, 2009 to Advisory Action mailed Mar. 12, 2009", 9 pgs.

"U.S. Appl. No. 11/456,942 Advisory Action mailed May 7, 2009", 6 pgs.

"U.S. Appl. No. 11/456,942, Final Office Action mailed Mar. 10, 2009", 15 pgs.

"U.S. Appl. No. 11/456,942, Response filed May 4, 2009 to Final Office Action mailed Mar. 10, 2009", 9 pgs.

"U.S. Appl. No. 11/456,942, Response filed Jun. 4, 2009 to Advisory Action mailed May 7, 2009", 10 pgs.

"U.S. Appl. No. 11/456,937, Final Office Action Mailed Dec. 22, 2008", 10 pgs.

"U.S. Appl. No. 11/456,937, Non-Final Office Action mailed Mar. 12, 2010", 9 pgs.

* cited by examiner

RF TELEMETRY LINK QUALITY ASSESSMENT SYSTEM AND METHOD

TECHNICAL FIELD

This disclosure relates generally to implantable medical devices and, more particularly, to systems and methods for assessing the quality of wireless communications with implantable medical devices.

BACKGROUND

Implantable medical devices (IMDs) include devices implanted in the human body to provide medical treatment. Examples include pacemakers and stents. A device exterior to the human body, called a programmer, is used to program an IMD.

Some programmers and IMDs communicate via radio frequencies (RF) using a wireless electrical connection. The quality of the wireless communication between the programmer and the IMD, whether in an operating room, an intensive care facility, a patient follow-up clinic, or home monitoring situation, may be compromised by causes such as interference from other RF sources and large transmission distance.

SUMMARY

Disclosed herein, among other things, is a method for assessing link quality for RF transmissions between a programmer and an IMD. An embodiment of the method includes measuring a plurality of available wireless communication channel potentially used to communicate between an implantable medical device (IMD) and a programmer to determine signal and noise levels for the channels. The method also includes storing the signal and noise levels. The method further includes processing the stored levels to determine the interference potential on the channels adjacent to the available channels. In this embodiment, the method also includes selecting a preferred communication channel based on a function of noise level for a target center channel and interference potential for corresponding adjacent channels to the target channel.

Various method embodiments include receiving a request for a link quality assessment from a programmer. The method also includes simulating an IMD in an RF session with the programmer over a plurality of available wireless communication channel potentially used to communicate between the IMD and the programmer. The method further includes testing the plurality of available wireless communication channels to record the presence of frame error rates, retries, and packet errors on the channels. In addition, the method includes selecting a preferred communication channel based on lowest error rates, retries and packet errors.

One aspect of this disclosure relates to a radio frequency link quality assessment device. According to one embodiment, the device includes an antenna and a communication circuit electrically connected to the antenna. The communication circuit is adapted to receive wireless communication between an implantable medical device and a programmer. The device also includes a processor electrically connected to the communication circuit. The processor is adapted to execute embedded instructions, to evaluate signal and noise strength of available wireless communication channels potentially used to communicate between the IMD and the programmer to determine respective signal and noise levels for the channels. The processor is also adapted to determine the interference potential on the channels adjacent to the available channels, and to recommend a communication channel based on a function of noise level for a target center channel and interference potential for corresponding adjacent channels to the target channel. The device further includes a memory electrically connected to the processor. The memory is adapted to store the embedded instructions, measurements of individual channels and results of evaluation.

Another aspect of this disclosure relates to a system for assessing link quality for RF transmissions between a programmer and an IMD. According to one embodiment, the system includes an implantable medical device and a programmer wirelessly coupled to the implantable medical device. The system also includes a radio frequency (RF) link quality assessment (LQA) device positioned to receive a radio frequency communication between the implantable medical device and the programmer. The RF LQA device includes an antenna and a communication circuit electrically connected to the antenna. The communication circuit is adapted to receive wireless communication between an implantable medical device and a programmer. The device also includes a processor electrically connected to the communication circuit. The processor is adapted to execute embedded instructions to evaluate signal and noise strength of available wireless communication channels potentially used to communicate between the IMD and the programmer to determine respective signal and noise levels for each channel. The processor is also adapted to determine the interference potential on the channels adjacent to each available channel, and to recommend a communication channel based on a function of noise level for a target center channel and interference potential for corresponding adjacent channels to the target channel. The device further includes a memory electrically connected to the processor. The memory is adapted to store the embedded instructions, measurements of individual channels and results of evaluation.

Various system embodiments include an implantable medical device and a programmer wirelessly coupled to the implantable medical device. The programmer includes an antenna and a communication circuit electrically connected to the antenna. The communication circuit is adapted to wirelessly communicate with the implantable medical device. The programmer also includes a processor electrically connected to the communication circuit. The processor is adapted to execute embedded instructions to evaluate signal and noise strength of available wireless communication channels potentially used to communicate between the IMD and the programmer to determine respective signal and noise levels for each channel. The processor is also adapted to determine the interference potential on the channels adjacent to each available channel, and to select a communication channel based on a function of noise level for a target center channel and interference potential for corresponding adjacent channels to the target channel. The programmer further includes a memory electrically connected to the processor. The memory is adapted to store the embedded instructions, measurements of individual channels and results of evaluation.

Various system embodiments include a means for measuring a plurality of available wireless communication channel potentially used to communicate between an implantable medical device (IMD) and a programmer to determine respective signal and noise levels for the channels. The system also includes a means for storing the signal and noise levels. The system further includes a means for processing the stored levels to sort the available channels by noise level, and for processing the stored levels to determine the interference potential on the channels adjacent to the available channels. In addition, the system includes a means for selecting a communication channel based on a lowest sum of noise level for a target center channel and interference potential for corresponding adjacent channels to the target channel.

This Summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

DETAILED DESCRIPTION

The following detailed description refers to the accompanying drawings which show, by way of illustration, specific aspects and embodiments in which the present invention may be practiced. The various embodiments are not necessarily mutually exclusive, as aspects of one embodiment can be combined with aspects of another embodiment. These embodiments are described in sufficient detail to enable those skilled in the art to practice the invention. Other embodiments may be utilized and structural, logical, and electrical changes may be made without departing from the scope of the present invention.

IMD/Programmer System

Figure 1:
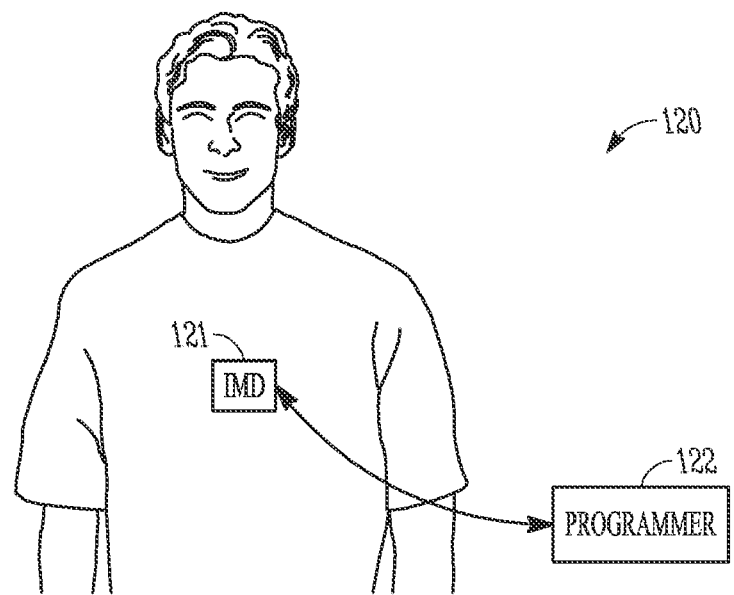
FIG. 1 illustrates a system including an implantable medical device (IMD) and a programmer, according to various embodiments.

FIG. 1 illustrates a system 120 including an implantable medical device (IMD) 121 and a programmer 122, according to various embodiments. Various embodiments of the IMD 121 include pulse generators such as cardiac rhythm management devices (with pacing and defibrillating capabilities) or neural stimulators, and various embodiments include a combination of neural stimulation and cardiac rhythm management functions. The programmer 122 and the IMD 121 are capable of wirelessly communicating data and instructions. In various embodiments, for example, the programmer 122 and IMD 121 use telemetry coils to wirelessly communicate data and instructions. The programmer and IMD use telemetry antennas to communicate, in various embodiments. Thus, the programmer can be used to adjust the programmed therapy provided by the IMD 121, and the IMD can report device data (such as battery and lead resistance) and therapy data (such as sense and stimulation data) to the programmer using radio telemetry, for example.

Figure 2:
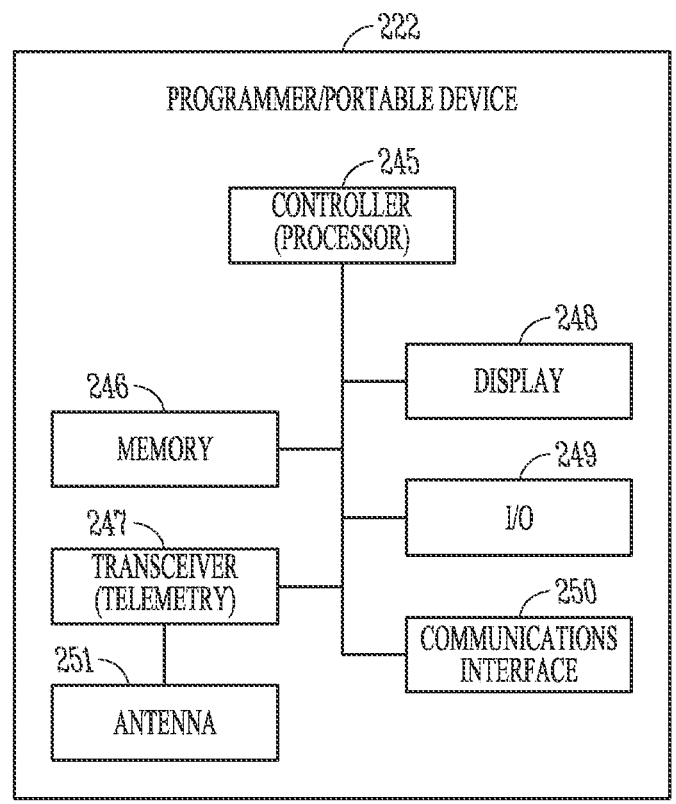
FIG. 2 illustrates a programmer such as illustrated in the system of FIG. 1 or other external device to communicate with the IMD(s), according to various embodiments.

FIG. 2 illustrates a programmer 222, such as the programmer 122 illustrated in the system of FIG. 1 or other external device to communicate with the IMD(s), according to various embodiments. An example of another external device includes Personal Digital Assistants (PDAs) or personal laptop and desktop computers in an Advanced Patient Management (APM) system. The illustrated device 222 includes controller circuitry 245 and a memory 246. The controller circuitry 245 is capable of being implemented using hardware, software, and combinations of hardware and software. For example, according to various embodiments, the controller circuitry 245 includes a processor to perform instructions embedded in the memory 246 to perform a number of functions, including communicating data and/or programming instructions to the implantable devices. The illustrated device 222 further includes a transceiver 247 and associated circuitry for use to communicate with an implantable device. Various embodiments have wireless communication capabilities. For example, various embodiments of the transceiver 247 and associated circuitry include a connection to a telemetry coil or antenna 251 for use to wirelessly communicate with an implantable device. The illustrated device 222 further includes a display 248, input/output (I/O) devices 249 such as a keyboard or mouse/pointer, and a communications interface 250 for use to communicate with other devices, such as over a communication network.

As mentioned above, the quality of the wireless communication between the programmer and the IMD, whether in an operating room, an intensive care facility, a patient follow-up clinic, or home monitoring situation, may be limited by causes such as interference from other RF sources and large transmission distance.

RF Link Quality Assessment Device

The disclosed RF link quality assessment (LQA) device is used assess the viability of a programmer/IMD telemetry link. By selecting the best available wireless communication channel between a programmer and an IMD, the quality of the telemetry transmission can be improved and the potential for lost signals ("drop-outs") can be reduced. While the following illustrations depict the LQA device as a stand-alone unit, the functionality described can be implemented within the programmer itself, as illustrated in FIG. 2 above.

Figure 3:
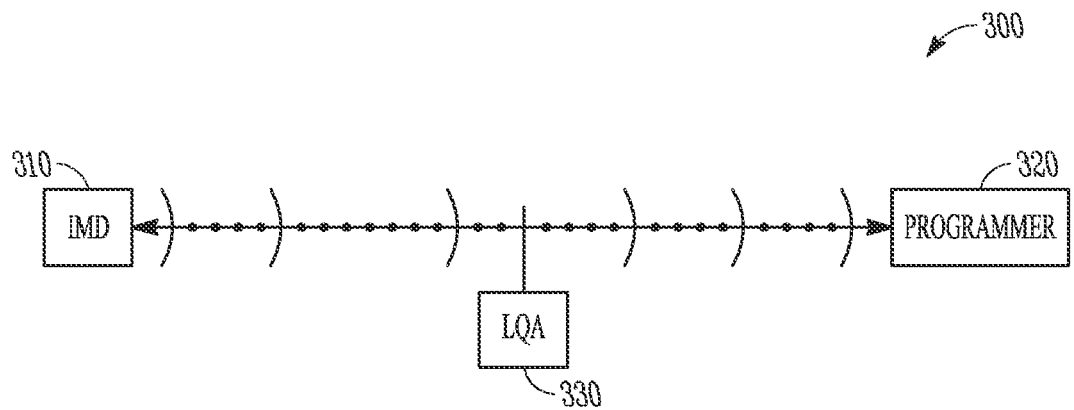
FIG. 3 illustrates a system including a RF link quality assessment device, a programmer and an IMD, according to various embodiments.

FIG. 3 illustrates a system including a radio frequency (RF) link quality assessment device, a programmer and an IMD, according to various embodiments. The system 300 includes a programmer 320 for wirelessly communicating with an IMD 310 and an LQA device 330. As described in more detail in FIG. 4 below, the LQA device includes a means for measuring a plurality of available wireless communication channel potentially used to communicate between an IMD and a programmer to determine respective signal and noise levels for the channels. In various embodiments, the measuring means include electronic circuitry adapted to measure signal and noise levels of RF communication channels. The device also includes a means for storing the signal and noise levels and a means for processing the stored levels to sort the available channels by noise level, and for processing the stored levels to determine the interference potential on the channels adjacent to the available channels, according to various embodiments. In various embodiments, the storing means includes computer memory and the processing means includes a processor. In addition, the device includes a means for selecting a communication channel based on a lowest sum of noise level for a target center channel and interference potential for corresponding adjacent channels to the target channel. In various embodiments, the selecting means includes a processor. As mentioned, the described means can be implemented within a stand-alone link quality assessment device, such as a hand-held device, or within the programmer. In this manner, the programmer system can prepare to change channels in response to interference.

Figure 4:
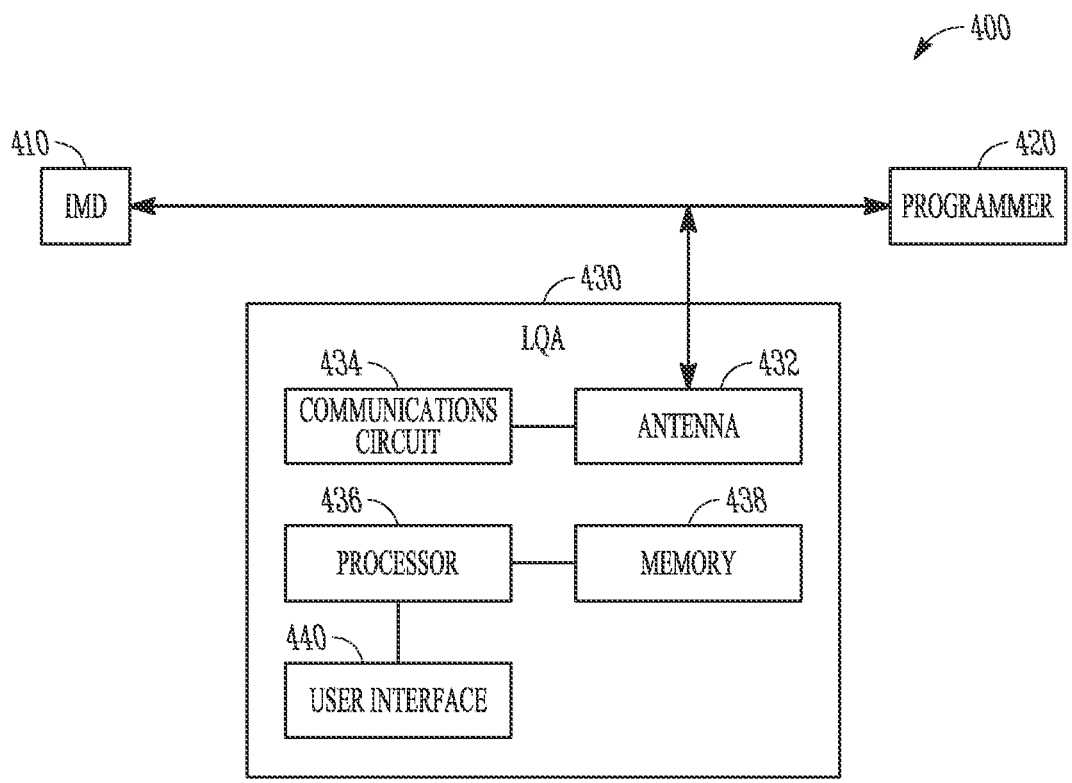
FIG. 4 illustrates a system for assessing link quality for RF transmissions between a programmer and an IMD, according to various embodiments.

FIG. 4 illustrates a system for assessing link quality for RF transmissions between a programmer and an IMD, according to various embodiments. The system 400 includes an implantable medical device 410 and a programmer 420 wirelessly coupled to the implantable medical device. The system also includes a radio frequency link quality assessment (LQA) device 430 positioned to receive a radio frequency communication between the implantable medical device and the programmer. The LQA device includes an antenna 432 and a communication circuit 434 electrically connected to the antenna. The communication circuit 434 is adapted to receive wireless communication between an implantable medical device and a programmer. The device 430 also includes a processor 436 electrically connected to the communication circuit 434. The processor 436 is adapted to execute embedded instructions to evaluate signal and noise strength of available wireless communication channels potentially used to communicate between the IMD and the programmer to determine respective signal and noise levels for the channels. In an embodiment, the processor evaluates the channels successively. The processor is also adapted to determine the interference potential on the channels adjacent to the available channels, and to select or recommend a communication channel based on a function of noise level for a target center channel and interference potential for corresponding adjacent channels to the target channel. In an embodiment, the illustrated LQA device 430 further includes a user interface 440, which may include a display, input/output (I/O) devices such as a keyboard or mouse/pointer, and a communications interface for use to communicate with other devices, such as over a communication network.

In an embodiment, the processor is adapted to sort the available channels by noise level. In various embodiments, the processor is adapted to sort the available channels by a lowest sum of the noise level on the target channel and the largest noise level of the two adjacent channels to the target channel. The device 430 further includes a memory 438 electrically connected to the processor. The memory 438 is adapted to store the embedded instructions, measurements of individual channels and results of evaluation.

According to various embodiments, the IMD 410 includes a pulse generator, such as a cardiac rhythm management device. Other types of IMDs are within the scope of this disclosure. As previously mentioned, the radio frequency LQA device 430 may be a handheld device. According to an embodiment, the LQA device is adapted to receive a request for an alternative communication channel from the IMD. In an embodiment, the communication circuit 434 includes a transmitter and a receiver. In another embodiment, the communication circuit 434 includes a transceiver.

The LQA device may also include a display electrically connected to the processor 436, in an embodiment. The display is adapted to provide a visual depiction of evaluation results, such as a graph of the peak or average noise measurement for each channel or of the calculated LQA for each channel. According to various embodiments, the LQA device is adapted to scan available successive wireless communication channel to measure noise level when a link between the IMD and the programmer is not in use. In an embodiment in which the LQA functionality resides within the programmer, the programmer is adapted to continue to scan available channels until the programmer is commanded to resume an existing telemetry session or establish a new telemetry session.

LQA at the IMD

In one embodiment, the programmer can request the Implantable Medical Device (IMD) to perform its own passive Link Quality Assessment (LQA). In this embodiment, the programmer can request the IMD, which may be located many feet away and be subject to different interference levels, to perform a frequency assessment at that location. A programmer performed LQA will measure the noise levels at the programmer's location, while the IMD performed LQA will measure the noise levels at the IMD's location. The frequency assessment may be requested to measure either just the primary frequency, or to perform a full sweep of all available frequencies.

The programmer can send a command to the IMD to perform the LQA test. The IMD receives the command and performs a passive LQA. In this mode, the IMD must be attentive to the primary frequency in anticipation of the programmer resuming telemetry or command features. For this mode the IMD would scan all available frequencies in a sequence that alternates with the primary frequency. The IMD would check the primary frequency first for programmer telemetry. If no telemetry is requested, the IMD would move to a test frequency and measure noise levels. The IMD would then return to the primary frequency and check for programmer telemetry. If no telemetry is requested, the IMD would switch to the next test frequency, take the noise measurements and return to the primary frequency. This process would continue until either the frequency scan is complete, primary telemetry is requested, or the system shuts down the telemetry link at the end of a session. When the measurement is complete, the IMD telemeters the data to the programmer, whereupon the programmer evaluates the data and factors the IMD data into the evaluation. In this evaluation, the programmer can evaluate channel noise both at its location and the IMD's location.

In another embodiment, the IMD can proactively telemeter the primary frequency noise level to the programmer for evaluation. In this embodiment the IMD measures the primary frequency noise level during a period when telemetry is not requested by the programmer. The IMD telemeters the data to the programmer, and the programmer takes the IMD noise measurement into account during any optimization. An example is when the programmer passive LQA measures a low noise level on the primary frequency but the telemetry link still yields a high number of errors. The programmer now has a noise status from the IMD in order to make a more informed decision to stay on the current frequency or move to another frequency based on the noise levels at both ends of the telemetry link.

According to various embodiments, the programmer can request the IMD to check a particular frequency prior to making a primary frequency change. The programmers passive LQA may recommend a quiet frequency but before making the change, the programmer requests the IMD to check the frequency noise level at the IMD's remote location. The IMD performs the noise measurement on the new frequency, returns to the primary frequency, and telemeters the results to the programmer.

Display of Noise Levels

Figure 5:
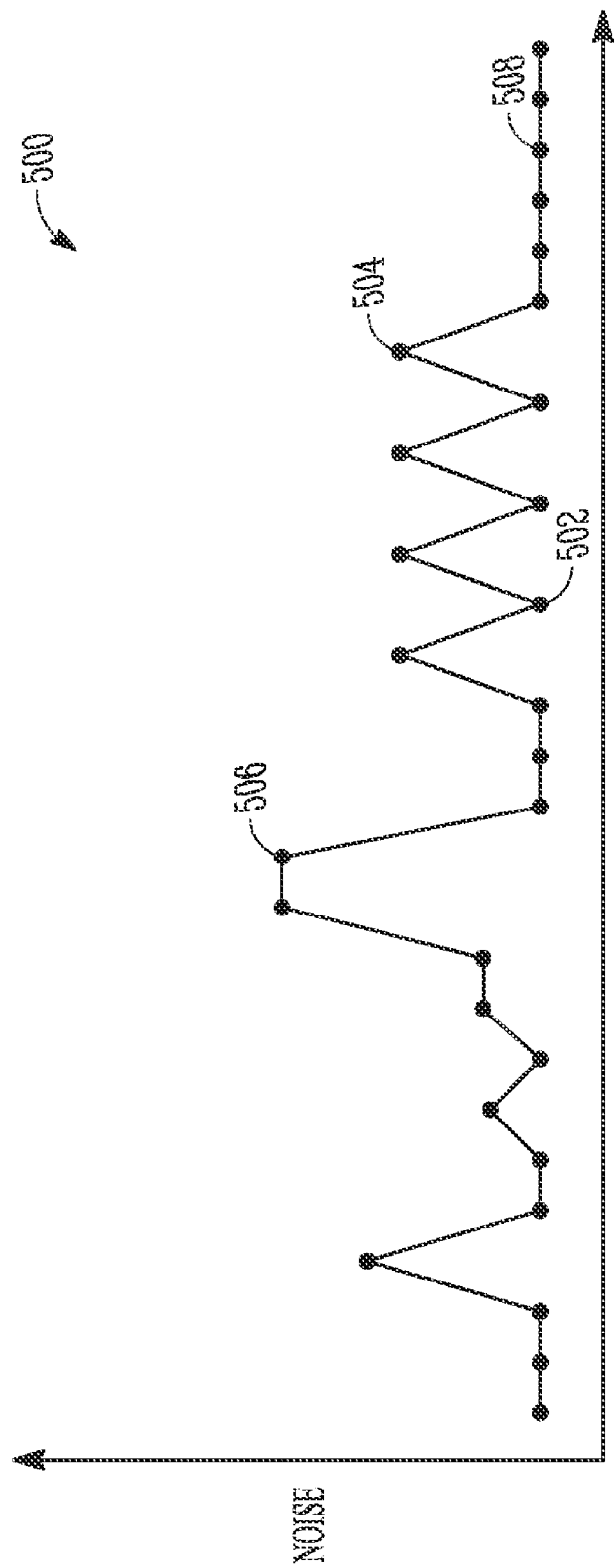
FIG. 5 illustrates a graphical display of noise levels on wireless communication channels potentially used to communicate between an IMD and a programmer, according to various embodiments.

FIG. 5 illustrates a graphical display 500 of noise levels on wireless communication channels potentially used to communicate between an IMD and a programmer, according to various embodiments. As discussed in detail with respect to FIG. 6 below, the disclosed method for assessing link quality proactively evaluates RF telemetry channel quality based on an evaluation of target channel noise levels and interference potential (or noise level) of channels adjacent the target channel. The wireless communication channel 502 has a relatively low noise level, but has adjacent channels with a high noise measurement. Wireless communication channel 504 has a relatively low adjacent channel noise measurement, but the channel itself has a high noise level. Communication channel 506 has both a high noise level and adjacent channels with high noise levels, making it the least desirable of the described channels. In contrast, communication channel 508 has both a low noise level and adjacent channels with low noise levels, making it the most desirable of the described channels.

Method for Assessing Link Quality

Figure 6:
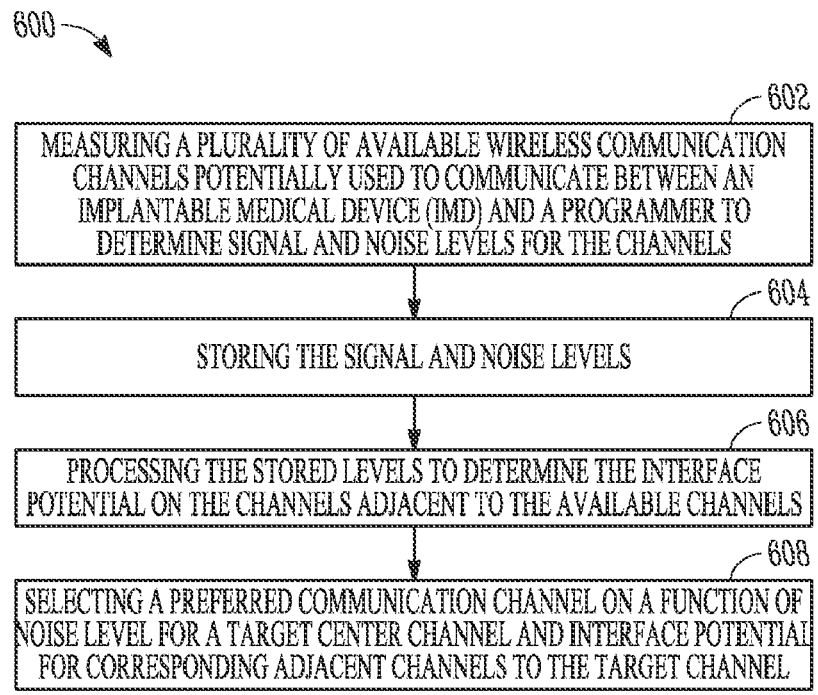
FIG. 6 illustrates a flow diagram of a method for assessing link quality for RF transmissions between a programmer and an IMD, according to various embodiments.

FIG. 6 illustrates a flow diagram of a method for assessing link quality for RF transmissions between a programmer and an IMD, according to various embodiments. The method 600 includes measuring a plurality of available wireless communication channels potentially used to communicate between an implantable medical device (IMD) and a programmer to determine signal and noise levels for the channels, at 602. The method also includes storing the signal and noise levels, at 604. In addition, the method includes processing the stored levels to determine the interference potential on the channels adjacent to the available channels, at 606. In this embodiment, the method also includes selecting a preferred communication channel based on a function of noise level for a target center channel and interference potential for corresponding adjacent channels to the target channel, at 608.

The method further includes processing the stored levels to sort the available channels by noise level, according to an embodiment. In various embodiments, the method includes sorting the available channels by a lowest sum of the noise level on the target channel and the largest noise level of the two adjacent channels to the target channel. Measuring the available wireless communication channels potentially used to communicate between an IMD and a programmer includes measuring each available successive wireless communication channel, according to an embodiment.

According to various embodiments of the method, an external hand-held instrument is used to measure the channels. The programmer is used to measure the channels, according to an embodiment. The programmer or the external hand-held device can have a display, or a display may reside in another location or device. According to various embodiments, numerical or graphical data is output to the display. Displayed data may include peak or average noise measurements for the channels, or a depiction of the sum of the noise level for each target channel and interference potential for corresponding adjacent channels to each target channel. Other types of data displays are within the scope of this disclosure.

According to various embodiments of the method, processing the stored levels to determine the interference potential on the channels adjacent to the available channels includes comparing noise levels for the adjacent channels to the target channels and selecting the highest of the noise levels to represent interference potential for the target channel. In one embodiment, the method selects a primary channel without using the adjacent channel measurements, relying only on the noise level for each target channel.

The disclosed method can be initiated by enabling a telemetry receiver on a first channel N, in an embodiment. A measurement of noise or signals on the channel is taken and stored. The next channel N+1 is evaluated in the same way, and this continues until all available channels have been measured. The sequence which the channels are evaluated can be varied. According to various embodiments, other sequences of evaluation are possible, for example N, N−1, N+1, N−2, N+2, etc. The resulting noise measurements are stored and available for recall and review by an operator.

Multiple algorithms can be applied to evaluate link quality and to yield a recommended primary frequency. A first algorithm sorts noise level measurements (X) for each channel in ascending order, with the lowest value having the highest link potential. A second algorithm determines the interference potential on channels adjacent to the potential primary channel. This algorithm examines noise levels on the channels on either side of the primary channel, and assigns a value (Y) corresponding to the highest of the two noise levels. According to various embodiments, other values for Y are assigned. Another algorithm uses the values of X and Y in some combination to evaluate the quality of the link. According to one embodiment, the sum X+Y for each channel is used to evaluate the quality of the link, with the lowest sum representing the highest link quality potential (or recommended primary frequency). Other embodiments used the product of X and Y or some other function of a center channel and at least one adjacent channel. In various embodiments, upon detection of unsuitable telemetry performance, telemetry frequency is shifted to the already determined recommended primary frequency. In addition, an evaluation can be made to determine if the lowest sum is within a range of noise parameters which will support RF telemetry, in an embodiment.

Method for On-Demand Assessment of Link Quality

Figure 7:
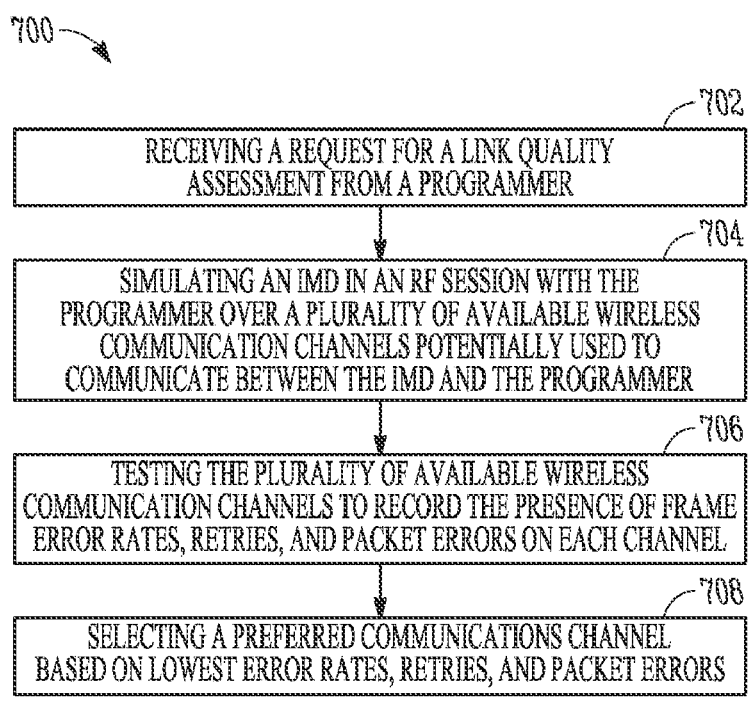
FIG. 7 illustrates a flow diagram of a method for on-demand assessment of link quality for RF communications between a programmer and an IMD, according to various embodiments.

FIG. 7 illustrates a flow diagram of a method for on-demand assessment of link quality for RF communications between a programmer and an IMD, according to various embodiments. The method 700 includes receiving a request for a link quality assessment from a programmer, at 702. The method also includes simulating an IMD in an RF session with the programmer over a plurality of available wireless communication channels potentially used to communicate between the IMD and the programmer, at 704. The method further includes testing the available wireless communication channels to record the presence of frame error rates, retries, and packet errors on the channels, at 706. In addition, the method includes selecting a preferred communication channel based on lowest error rates, retries and packet errors, at 708.

According to various method embodiments, testing the plurality of available wireless communication channels includes testing each available successive wireless communication channel. In an embodiment, simulating an IMD in an RF session with the programmer includes telemetering electrograms to the programmer. Testing the available wireless communication channels includes collecting link protocol data, according to one embodiment. Selecting a preferred communication channel may include executing an algorithm to assess performance of the available channels or to assess performance of adjacent channels to the available channels, in various embodiments.

As the method includes a simulated RF session, a preliminary indication of link quality can be assessed by observing the visual quality of the programmer display. In one embodiment of the method, the LQA can operate in the background of an actual programmer/IMD telemetry session by monitoring errors and retries. The disclosed method can be implemented before implantation of an IMD, or when evaluating an environment for its suitability for RF telemetry.

One of ordinary skill in the art will understand that the modules and other circuitry shown and described herein can be implemented using software, hardware, and combinations of software and hardware. As such, the illustrated modules and circuitry are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. A method, comprising:
   measuring a plurality of available wireless communication channels potentially used to communicate between an implantable medical device (IMD) and a programmer to determine signal and noise levels for the plurality of channels;
   storing the signal and noise levels;
   processing the stored levels to determine an interference potential on the channels adjacent to the available channels;
   performing a link quality assessment (LQA) for each of the plurality of available wireless communication channels, wherein the LQA includes, for each channel analyzed as a target channel, using the noise level for the target channel and interference potential for corresponding adjacent channels to the target channel as inputs to a function to provide a value for the LQA for the target channel; and
   selecting a preferred communication channel based on the LQA for each of the plurality of available wireless communication channels.

2. The method of claim 1, wherein measuring the plurality of available wireless communication channels potentially used to communicate between an IMD and a programmer includes measuring each available successive wireless communication channel.

3. The method of claim 1, further comprising:
   processing the stored levels to sort the available channels by noise level.

4. The method of claim 1, wherein performing the link quality assessment (LQA) and selecting the preferred communication channel includes:
   for each target channel, the function includes calculating a sum of the noise level for the target channel plus a largest noise level for corresponding adjacent channels to the target channel; and
   selecting the target channel with lowest sum as the preferred communication channel.

5. The method of claim 1, wherein measuring a plurality of available wireless communication channel potentially used to communicate between an IMD and a programmer includes using an external hand-held instrument to measure the channels.

6. The method of claim 1, wherein measuring a plurality of available wireless communication channel potentially used to communicate between an IMD and a programmer includes using the programmer to measure the channels.

7. The method of claim 1, wherein measuring a plurality of available wireless communication channel potentially used to communicate between an IMD and a programmer includes using the IMD to measure the channels.

8. The method of claim 1, wherein selecting a preferred communication channel includes outputting numerical data to a display.

9. The method of claim 1, wherein selecting a preferred communication channel includes outputting graphical data to a display.

10. The method of claim 9, wherein outputting graphical data to a display includes outputting a graph of peak noise measurement for the channels.

11. The method of claim 9, wherein outputting graphical data to a display includes outputting a graph of average noise measurement for the channels.

12. The method of claim 9, wherein outputting graphical data to a display includes outputting a graph of a sum of noise level for each target channel and interference potential for corresponding adjacent channels to each target channel.

13. The method of claim 1, wherein processing the stored levels to determine the interference potential on the channels adjacent to the available channels includes comparing noise levels for the adjacent channels to the target channels and selecting highest of the noise levels to represent interference potential for the target channel.

14. A system, comprising:
    means for measuring a plurality of available wireless communication channels potentially used to communicate between an implantable medical device (IMD) and a programmer to determine respective signal and noise levels for the channels;
    means for storing the signal and noise levels;
    means for processing the stored levels to sort the available channels by noise level, and for processing the stored levels to determine the interference potential on the channels adjacent to the available channels; and
    means for selecting a communication channel based on a lowest sum of noise level for a target center channel plus interference potential for corresponding adjacent channels to the target channel.

15. The system of claims 14, wherein the means for processing the stored levels includes a microprocessor located within a hand held link quality assessment device.

16. The system of claims 14, wherein the means for processing the stored levels includes a microprocessor located within the programmer.

17. A method, comprising:
measuring a plurality of available wireless communication channels potentially used to communicate between an implantable medical device (IMD) and a programmer to determine signal and noise levels for the plurality of channels;
storing the signal and noise levels;
processing the stored levels to determine an interference potential on the channels adjacent to the available channels;
evaluating each of the plurality of channels using noise levels for a target channel and interference potential for at least two channels adjacent the target channel; and
selecting a preferred communication channel based on a lowest sum of the noise level for the target center channel plus a largest noise level for corresponding adjacent channels to the target channel.

18. The method of claim 17, wherein processing the stored levels to determine the interference potential on the channels adjacent to the available channels includes comparing noise levels for the adjacent channels to the target channels and selecting highest of the noise levels to represent interference potential for the target channel.

19. The method of claim 17, wherein measuring the plurality of available wireless communication channels potentially used to communicate between an IMD and a programmer includes measuring each available successive wireless communication channel.

20. The method of claim 17, wherein selecting a preferred communication channel includes selecting a communication channel having both a relatively low noise level and adjacent channels with relatively low noise levels.

* * * * *